United States Patent
Schuldt et al.

[11] Patent Number: 5,478,235
[45] Date of Patent: Dec. 26, 1995

[54] DENTAL IMPRESSION TRAY

[75] Inventors: Harry J. Schuldt, 2861 SW. Lake Ter., Palm City, Fla. 34990; Donald P. Jochum, 1359 NW. Lakeside Trail; Allan J. Jochum, 1825 NW. Fork Rd., both of Stuart, Fla. 34994; Steven R. Jefferies, Milford, Del.

[73] Assignees: Harry J. Schuldt, Palm City; Donald P. Jochum; Allan J. Jochum, both of Stuart, all of Fla.

[21] Appl. No.: 148,754

[22] Filed: Nov. 5, 1993

[51] Int. Cl.⁶ ................................. A61K 9/00
[52] U.S. Cl. ..................................... 433/37
[58] Field of Search ................... 433/43, 44, 45, 433/46, 47, 48, 37, 38, 40, 41, 42, 214

[56] References Cited

U.S. PATENT DOCUMENTS

| | | | |
|---|---|---|---|
| 90,802 | 6/1969 | Wuestenberg | 433/37 |
| 1,509,377 | 9/1924 | Rodgers | 433/37 |
| 2,312,171 | 2/1943 | Jochum | 433/35 |
| 2,587,782 | 3/1952 | Stark | 433/48 |
| 2,758,374 | 8/1956 | Fisher et al. | 433/37 |
| 2,827,899 | 3/1958 | Altieri | 433/37 |
| 3,878,610 | 4/1975 | Coscina | 433/37 |
| 4,100,678 | 7/1978 | Yatabe | 433/9 |
| 4,530,662 | 7/1985 | Andersson et al. | 433/37 |
| 4,553,936 | 11/1985 | Wang | 433/37 |
| 4,867,682 | 9/1989 | Hammesfahr et al. | 433/37 |

FOREIGN PATENT DOCUMENTS

| | | | |
|---|---|---|---|
| 1037866 | 9/1953 | France | 433/37 |
| 9112777 | 9/1991 | WIPO | 433/214 |

OTHER PUBLICATIONS

Page from text "The Working Cast".
IDE Interstate DENTAL CATALOG, Fall 1987 cover sheet and p. 123.
ULTRADENT® STAINLESS TRAYS Pamphlet 3 pages.
Surfanalyzer® 5000/400; Advanced Surface Metrology Program Pamphlet, 4 pages.

*Primary Examiner*—Cary E. O'Connor
*Attorney, Agent, or Firm*—James B. Bieber; Edward J. Hanson, Jr.

[57] ABSTRACT

A dental impression tray having a rough textured surface which provides a multiplicity of pits made up of valleys and peaks, holes that don't penetrate through the tray, cavities, craters, crevices, ledges and/or undercuts which retain and/or stabilize the impression material. The rough textured surface of the handle provides a non-slip surface for a gloved hand.

14 Claims, 5 Drawing Sheets

DENTAL IMPRESSION TRAY

BACKGROUND OF THE INVENTION

The present invention relates to dental impression trays and more in particular to improvements in retention of impression materials in the dental impression trays.

Accurate replication of the teeth and surrounding soft tissues is the primary goal of taking an impression. A dental impression tray should retain the impression material when it is withdrawn from the patient's mouth. If the impression material remains in the mouth when the impression tray is withdrawn, the impression is generally ruined and useless. If the impression material comes loose from any part of the tray, but remains in the tray, the impression will usually be inaccurate. Any flexing or movement of the impression tray during the cure of the impression material generally distorts the impression.

Previously, many mechanical and some adhesive means of retaining the impression material in the impression tray have been employed. Carl Jochum and Harry Schuldt, fathers of three of the inventors, patented the first water-cooled impression tray, U.S. Pat. No. 2,312,171, in 1943. It used a perforated metal liner to retain the impression material. Subsequently, they used a peripheral rim and a horse-shoe shaped wire on the palate area to retain the impression material. These methods work, as is evidenced by the fact the company they founded still manufactures these trays today, but they are expensive and labor intensive to manufacture. To retain the impression material, some dental impression trays use holes, grooves, raised pedestals, serrations, barbs, or grid-like linings. Other impression trays use peel and stick adhesives, adhesive felt-like pads, spray-on adhesives, or brush-on adhesives. These methods work to varying degrees. Some are complex and difficult to manufacture and some require expensive or messy adhesives. The number and scope of the methods employed to retain the impression material in the impression tray proves that until now, retaining the impression material in the dental impression tray has not been easy to accomplish.

It has been known to "sand" blast brass dental impression trays to remove debris and roughness from their surfaces which were residues of manufacture. This was the opposite of the current invention where the sandblasting is not a smoothing procedure because of the manner in which it is carried out, but a rough texturing procedure. The brass offers a harder surface than aluminum and the treatment was with glass beads. The treatment was done by hand aiming straight at the surface to be treated. However, the end surface appearance was satiny, not unlike the matte finish of the aluminum trays of the present invention. In particular because of the straight-on application of the glass beads rather than the tumbling application of the abrasive of the current invention and the hardness of the brass surface as compared to aluminum, the indentations would not, it is believed, be substantively characterizable as undercut. In another brass prior art dental impression tray which had a large rim to retain the dental impression mold, a roughed finish was provided to the inside by sandblasting with a coarse sand the interior surfaces of the tray in the same basically straight-on fashion as described for the glass bead treatment. The roughened finish was macro-visible to the unaided eye in its uneven surface characteristics.

The dental impression tray in perhaps its most classic form is preferably curved sufficient to receive at least a partial arch-shaped group of teeth and channel-shaped in cross-section and wider than the teeth to be received therein. The channel-shaped cross-section provides a recess adapted to hold an approximate predetermined amount of the dental impression material for forming the impression of exposed surfaces of teeth or dental surfaces of the dentition including the surrounding mucosa therein.

The present invention is directed to providing dental impression trays of conventional designs with a microscopicly rough texture to the surfaces that are to be most directly contacted by the dental impression material with a need to retain or hold the dental impression material in positive position after the impression of the dentition has been taken. By microscopic it is meant that the texture is so fine or small that its specific roughening structure cannot be readily distinguished without the use of a microscope. The surface, in its preferred formats will appear matte or dull rather than shiny, smooth and/or polished, but the character of the roughing is indistinguishable as to its detail without microscopic examination. In preferred formats the microscopic rough texture has a substantial occurrence of undercuts in the surface so that the dental impression material is not only retained by normal surface adhesion caused by the increase in surface area but also by being trapped under the undercut overhang.

An object of the invention is to provide a dental impression tray of simple construction adapting it for use with various types of dental impression materials.

Another object is to provide a dental impression tray that provides efficient retention of various dental impression materials.

A further object is to provide a dental impression tray of simple construction with the surface of the handle modified in such a way as to provide a non-slip surface for the gloved hand of a Dentist or Dental Assistant using the dental impression tray.

DETAILED DESCRIPTION OF THE PREFERRED EMBODIMENT OF THE INVENTION

Figure 1:
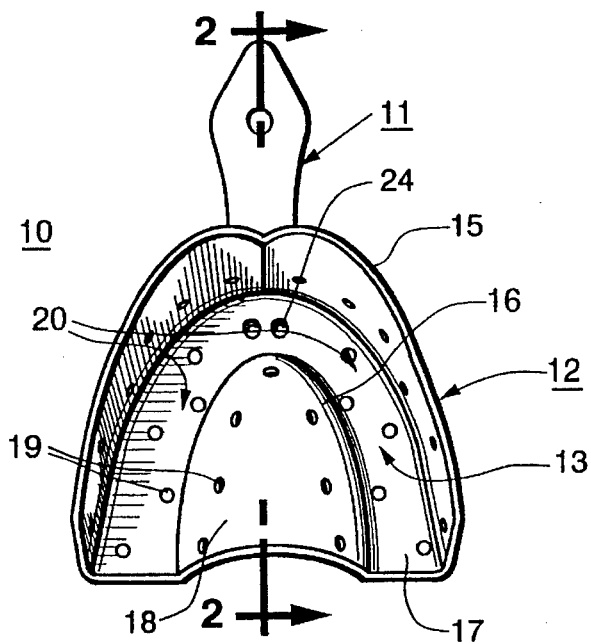
FIG. 1 is a plan view of one embodiment of the impression tray of the present invention for taking the full upper arch of dentition.

Looking at FIG. 1, it is to be understood that the substantially U shaped full arch dental tray shown is exemplary. The tray 10 illustrated is in a maxillary configuration specifically intended for preferably taking the upper, maxillary portion of the oral cavity of a dental patient. It will be understood that the tray after being filled with unset dental impression material is inserted into a patient's mouth and positioned below the upper arch of dentition and then pressed upward to force the impression material to flow into as exact conformity to the maxillary portion of the oral cavity and its dentition as possible. The tray retains and directs the flow of the impression material about the area of the oral cavity being taken in conventional manner.

Figure 2:
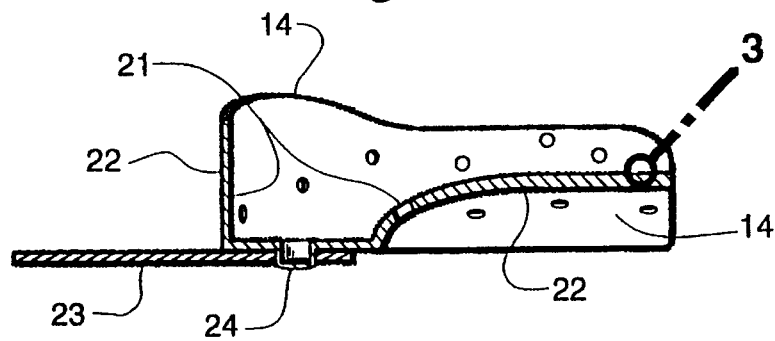
FIG. 2 is a schematic longitudinal sectional view taken on the line 2—2 of FIG. 1.

Looking at FIGS. 1 and 2, the dental tray 10 is shown with a handle 11 and a body 12. The body 12 has an inside body portion 13 for containing the dental impression material and an outside body portion 14. This portion 13 is defined by the inside of the projecting outer side wall 15 and the inside of the inner side wall. These side walls 16 extend respectively from opposite sides of the inside of the bottom wall 17. The wall 16 continues across the palate area 18 bridging the U in the bottom wall 17. The walls 15 and 16 respectively form the U shaped recess 20. The wall 15 projects away from the bottom wall 16 at a varying angle of approximately 80° to 90° and the bottom wall would therefore be at a 0° angle from this perspective. It will be understood that the "bottom" wall is a term used in the orientation shown and for a lower arch dental impression tray would equally apply, with the tray being understood to then be turned over from its position of use of application over the lower tooth arch in the oral cavity where the tray opening would face down.

Perforations 19 are shown in FIG. 1. These perforations or holes are conventional means known in the art for retaining the dental impression material in positive locked relation with the dental impression tray after the dental impression material has set. These holes may typically be spaced approximately 6 holes per square inch and extend through the wall areas of the tray that are intended to be in contact with the dental impression material when a dental impression is taken. A review of a sampling of dental impression trays reveals spacing between such holes of 0.31–0.58 inches apart. The holes may typically be approximately 3/32 inch in diameter and round or oval. However, there is no standard for the holes per square inch or hole size or shape.

Figure 3:
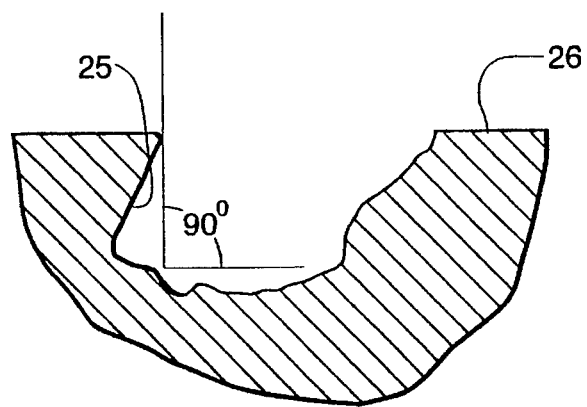
FIG. 3 is an enlarged schematic sectional view taken on line 3—3 of FIG. 2 and broken away to allow increased enlargement.

Looking now in particular at FIGS. 2 and 3, the impression material retaining surfaces 21 of the dental tray are rough textured as schematically illustrated. In a preferred embodiment all of the surfaces of the dental tray that are inside the body of the tray and in intended contact with the dental impression material have a retention rough texture.

Depending on the degree of retention properties supplied to the retention rough texture, the retention rough texture may further stabilize the set impression against distortion, thereby improving the accuracy of the final dental prostheses or dental appliance that is to be made utilizing the impression or the retention rough texture will serve as the sole impression material retainer mechanism.

In the embodiment shown in FIGS. 1–3 the retention rough texture retention properties are sufficient to be the sole impression material retainer. In some preferred embodiments the rough texture retention properties are the sole impression material retainer. The perforations serve as an adjunct to assure good retention of the set impression material should the rough textured surface be damaged or contaminated or should some extraordinary stress be applied to the set dental impression material and/or the dental impression tray. Of course, in combination both the rough texture and the perforations serve to stabilize the dental impression against distortion and to lock the set impression material and the tray together.

As a convenience in manufacture, and in some special instances for additional reasons in some preferred embodiments, all of the surfaces of the body of the dental impression tray are rough textured as at 22. In some preferred embodiments the handle 11 is also provided with a rough texture as at 23 to provide a non-slip surface for a gloved hand. A bradding 24 of the handle 11 to the body 12 is shown in FIGS. 1 and 2.

The rough textured surface provides an increase in surface area which increases the surface available for retention of the cured and set impression material. This provides good surface adhesion because of the increase in surface area. The preferred rough textured surface of the present invention is a micro pitted surface. By a micro pitted surface with retention features, it is meant a surface having microscopic valleys and peaks, undercuts, cavities, craters, crevices, ledges and/or holes that don't penetrate through the tray and that serve an impression material retention function, stabilizing the dental impression at the interface between the impression material and the dental impression tray.

Referring to FIG. 3, the more preferred embodiments provide micro undercuts 25, where there is an overhang by which the impression material, before curing, can flow into the pitted surface, under the overhang, providing a portion that must either be broken or ripped off or snapped from under the overhang. By undercut is meant an overhang portion projecting under the general plane 26 (the actual plane being irregular, the general plane 26 is theoretical) of the impression tray retaining surface 21 that resists the withdraw of the impression material from the tray. Rough textured surface includes overhangs and undercuts. Preferably substantially all of the pits have a breadth at the tray surface in their smallest diameter of no more than about 100 microns and more preferably on the order of 1–100 microns with an allowance for inconsistences due to scratches and the like and the lack of exact precision in present manufacturing procedures.

As used in this application micro mechanical retention and micro mechanical interlock mean that there are overhang areas or pitted areas that do not open at an angle of 90° or more to the general plane but at an angle of less than 90° to the general plane and the dental impression material after curing is caught or trapped under or by the overhang, see FIG. 3. The "undercut" may not actually be cut or etched under the surface but can be formed by flow or bending the edge of a pit over the pit when examined from straight-up 90° from the surface.

Of course in other preferred embodiments retention rough textured surfaces may be used with other retention means than the perforation holes 19 shown in FIG. 1. Such other additional means are by way of example, the beaded outer edges which are present on the trays sold by the Caulk Division of Dentsply International Inc. under the tradename RIM-LOCK®.

In another preferred embodiment, not shown, the inside of the body has a rough texture and the outside of the body has a smooth texture. Thus the inside of the body has a retention rough surface to retain the cured, set dental impression material and the outside of the body has a non-retention smooth texture to facilitate non irritating insertion in the patient's mouth and resist retention of extraneous foreign material.

It is recognized that the difference between smooth texture and rough texture is relative and it is meant to convey this difference in one parameter by the profilometer test set forth in EXAMPLE 2. For preferred embodiments of the invention the reading should be an Ra of at least 2, more preferably 3 and most preferably 4.

The rough textured surface can be provided in many ways. The most preferred manner is by "sand" blasting in a manner providing undercuts. The rough surface can be provided in other ways such as mechanically abrading prior to stamping or forming or after stamping or forming if the tray is cast by coating the inside of the casting mold with a rough coating that can be washed from the surface of the casting with water or by scrolling with a laser or acid etching. Preferably the rough texture is random but in some other preferred embodiments it may have a pattern, or it can be random rough textured in a pattern.

The preferred material of construction is malleable metal. Preferably the metal is readily malleable and aluminum is most preferred. Such a preferred tray is the tray of EXAMPLE 1 of the present invention. Aluminum is also preferred because it is so readily recyclable and is of substantial economic and environmental merit as well as being light weight. Other less preferred materials may be beneficially employed in some instances. Such other materials by way of example only are plastic, ceramic and other metals such as steel.

To use the dental impression tray of the present invention no preparation, such as application of an adhesive to the impression material receiving portion of the inside of the tray body is required or desirable. A selected dental impression material, which by way of example could be alginate, polyether or polysiloxane or the like is placed in the tray in the manner desired by the Dentist or Dental Assistant and the tray is inserted into the patient's mouth in conventional manner.

By an aspect of the present invention a method of forming a dental impression in polymerizable flowable dental impression material capable of being rendered permanently elastomeric to form a mold shape having a memory is provided. The method includes the steps of: placing a predetermined quantity of said flowable material in a dental impression tray having walls defining a recess, said walls comprising microscopically roughened texture; inserting said impression tray in the oral cavity and impressing said material in said tray against dental anatomy in the oral cavity of which a mold is desired; after said dental impression material has been rendered to a permanently elastomeric mold, removing said mold from the oral cavity bound by said microscopically roughed texture of said walls of said dental impression tray.

In one preferred embodiment the tray is a single use tray, being reasonably inexpensive to manufacture especially when made of the preferred material for construction, aluminum. A single use tray eliminates expensive time consuming clean up and sterilization procedures preventing infectious cross contamination between patients and operatory personnel. However, in other preferred embodiments the dental impression tray may be a limited use tray, suitable for a limited number of uses such as 5 or 10 before losing its superior retention properties or an extended use tray. Preferably the dental impression tray is rigid, thus avoiding deforming of the impression when the dental impression in the tray is removed from the patient's mouth for further processing.

The invention is further illustrated by the following examples.

EXAMPLE 1

A number of dental impression trays configured as shown in FIGS. 1 and 2 and also configured for the lower arch (not shown) were formed from aluminum sheet 1100–0 Temper of 0.040 inch, 18 gauge, by stamping in a machined punch and dye mounted on a two-post die set and formed on a 28 ton OBI punch press. The handle 11 is secured to the body 12 by two punched button clinches, a cold formed joint created by using a punch and die so that the lower layer of metal locks around the upper layer. The perforations 19 (FIG. 1) were 3/32 inch holes with an average frequency spacing of 6 holes per square inch.

Several trays were retained in this condition and other trays were provided with dental impression retention characteristics of the present invention by sand blasting the entire tray after the handle 10 had been interlocked with the body 12. The abrasive blasting was done with a 5/16" Tungsten carbide nozzle using 60 grit aluminum oxide at 50 psi pressure, at approximately 10" from the trays being treated which were in a rotating basket. The speed of the basket rotation was 2 revolutions per minute, the size of the basket was 12 inches in diameter, and the length of time was 10 minutes. The number of trays in the basket was 20.

Two lower arch trays that were not sand blasted were sectioned across the tray through the surface of the floor, bottom wall 17, FIG. 1, on a diamond wafering saw. Using a Scanning Electron Microscope (SEM), model 40, International Scientific Instruments, Inc., Pleasanton, Calif., the sections at the impression material retaining surface 21 (FIG. 2) were photographed. The photographs were taken at an accelerator voltage of 15 KV, using a split magnification of 500/1500×; a Secondary Electron detector, a tilt angle of 40° and uncoated. They are shown in FIGS. 4 and 5 respectively.

It will be seen that the surfaces are basically smooth and untextured, although the surfaces are not highly polished to eliminate some degree of surface irregularity inherent to the usual manufacture. It cannot be said that there would not be any occurrence of overhang at the surface but basically the surface is left smooth in the sense of typical untextured manufacture.

Figure 4:
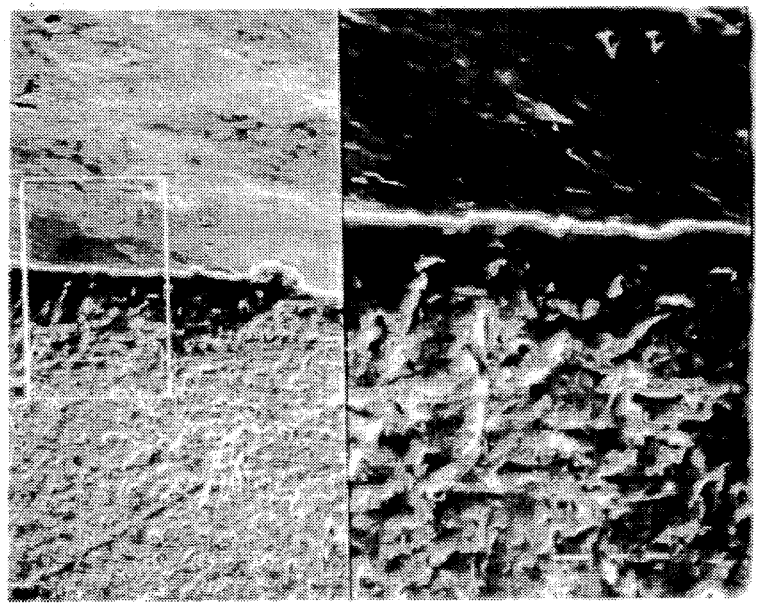
FIGS. 4 and 5 are photomicrographs of sections through untextured areas of dental impression trays showing the untextured surface.
Figure 5:
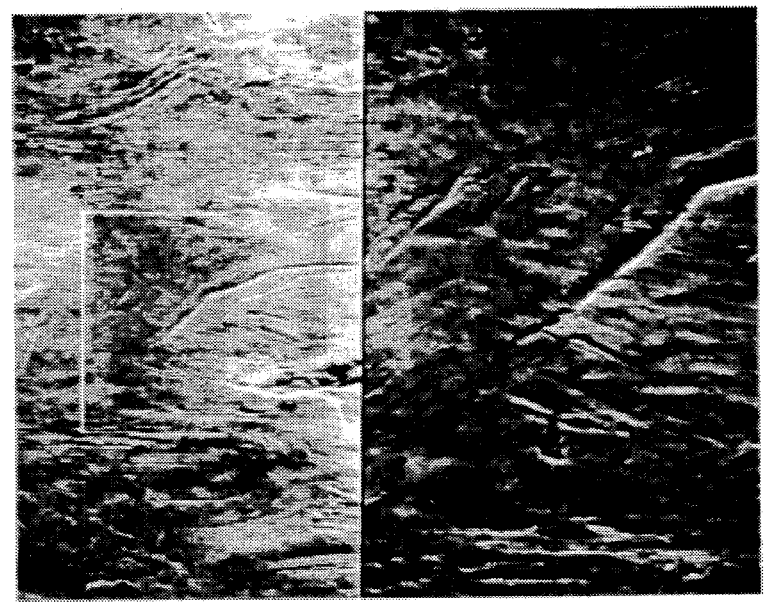
Figure 6:
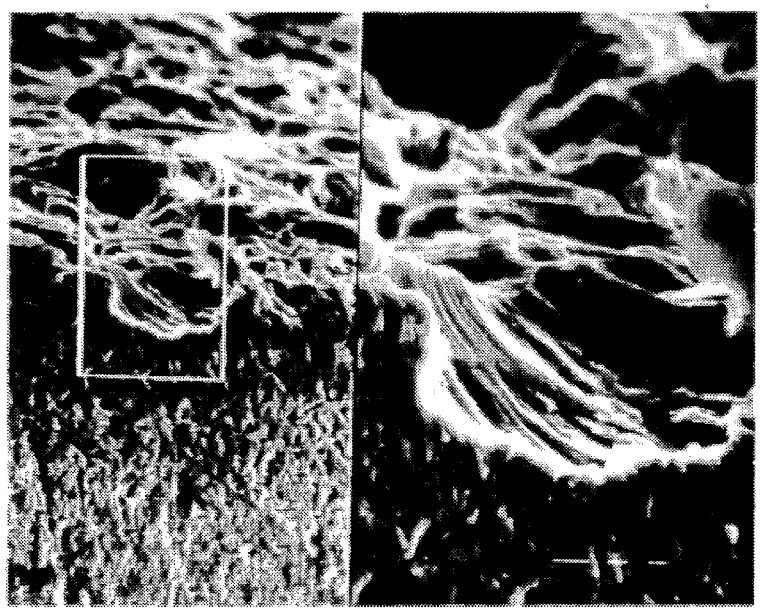
FIGS. 6–9 are photomicrographs of sections through textured areas of dental impression trays of the present invention showing the textured surface.
Figure 7:
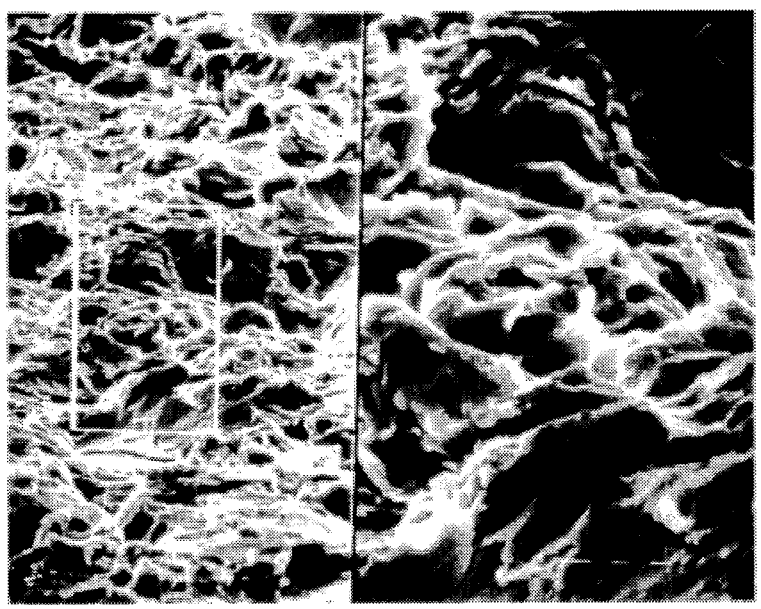
Figure 8:
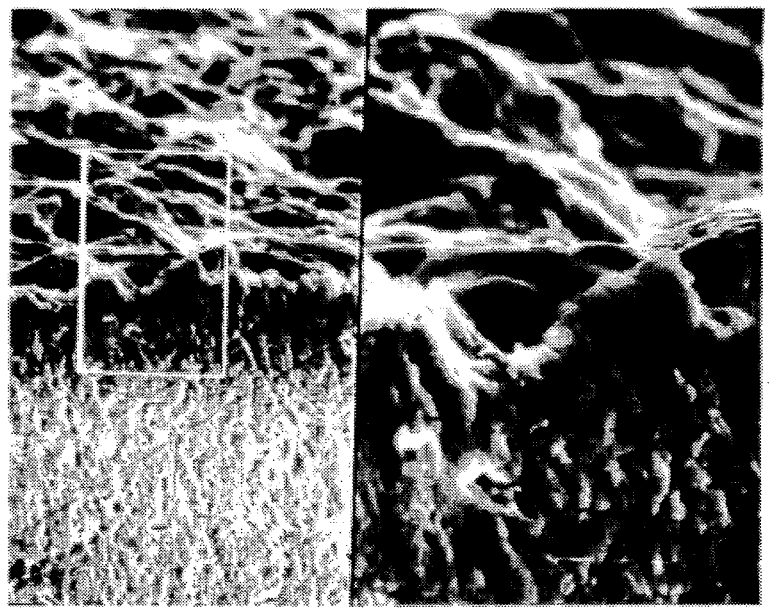
Figure 9:
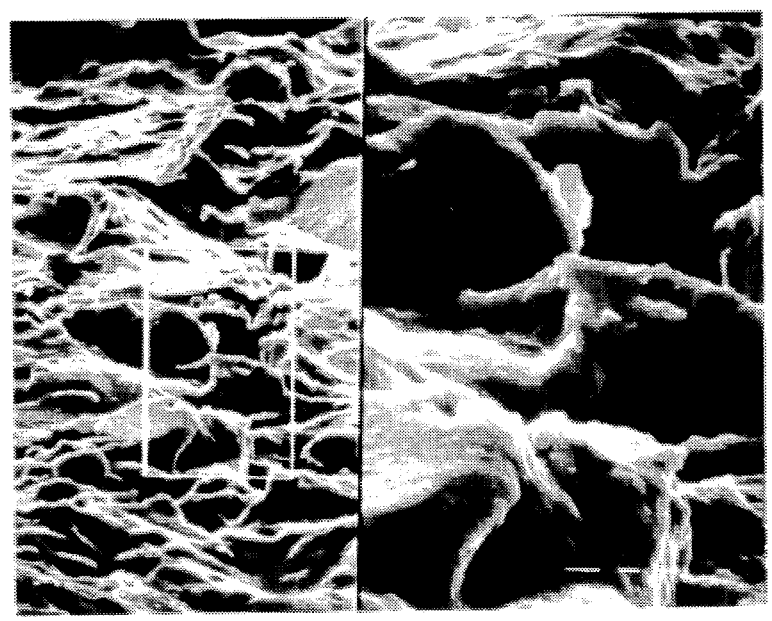

FIGS. 6–9 are SEMs prepared as described for FIGS. 4 and 5, but of lower arch dental impression trays that had been sand blasted. Each SEM photograph is of a different tray section. The contrast between the untextured surfaces photographed and shown in FIGS. 4 and 5 and the textured surfaces of the invention shown in FIGS. 6–9 is clear.

Figure 10:
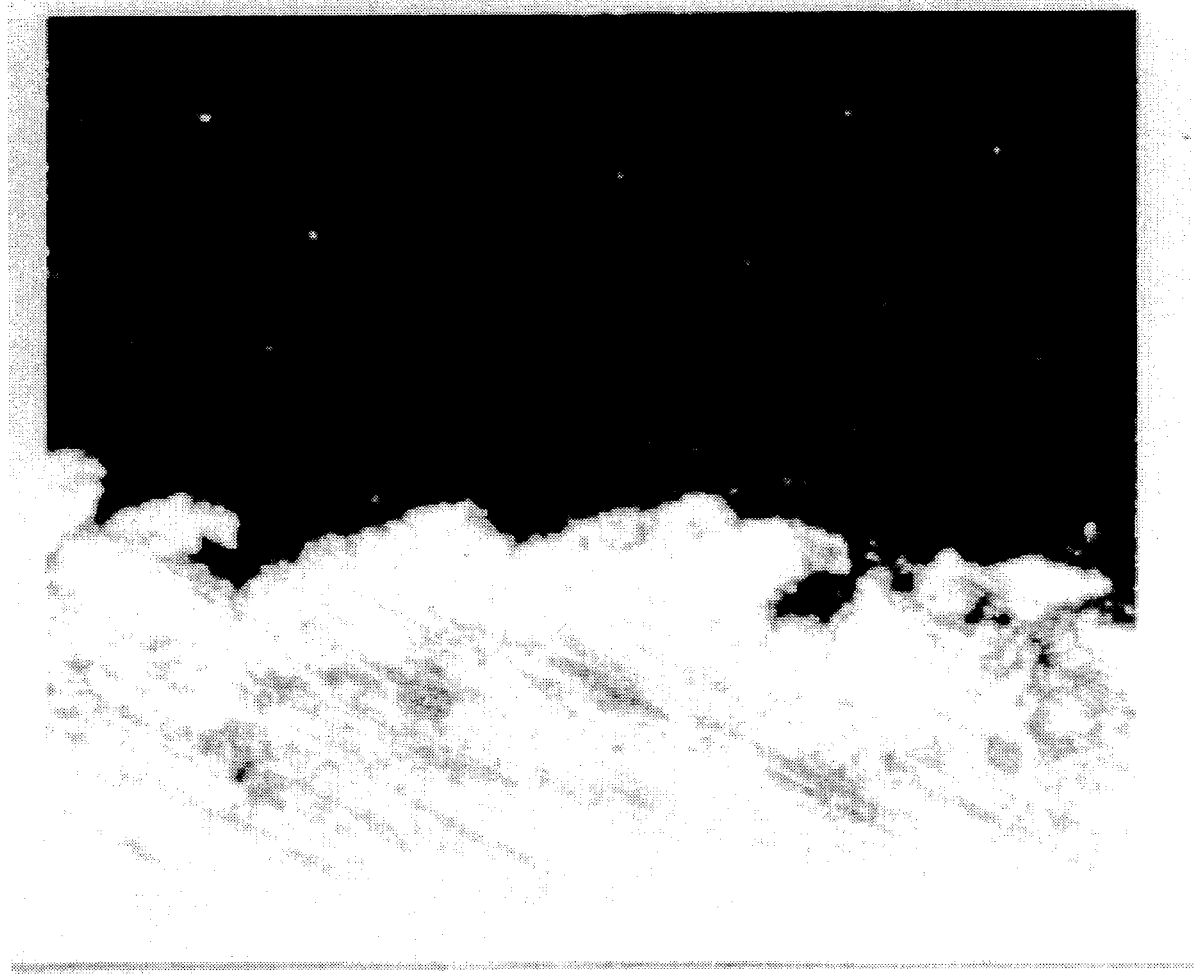
FIG. 10 is a photomicrograph of a section through a textured area of a dental impression tray of the present invention with a model impression of dental impression material shown bound in position in the tray.

FIG. 10 is a photograph using a Nikon optical microscope at 200× magnification. The tray was a lower arch tray containing a dental mold sectioned about 3 mm thick on a diamond wafering saw. The dental impression mold was formed of dental impression material bound in micro mechanical interlock by the texture, especially the undercuts as well as other pits. Notice the integrity of the interface and that no lift off or separation can be seen between the cured dental impression material and the texture of the dental impression tray.

The dental impression material was Reprosil® Quixx™ Putty vinyl polysiloxane impression material, a product of the L. D. Caulk Division of Dentsply International Inc. The mold was prepared by placing the uncured dental impression material in the dental impression tray, seating the tray over the lower arch in an oral cavity (mouth) of a human and curing for 6 minutes. The tray with attached dental mold was then withdrawn from the mouth and sectioned as described. The photograph is of the interface area of the dental impression material and the textured portion of the tray surface that is the retaining surface.

EXAMPLE 2

The aluminum sheet stock of EXAMPLE 1 was tested, both untreated and treated as described in EXAMPLE 1, but without either having been formed into a tray. The roughness of the surface was measured using a profilometer, Surfanalyzer® 5000/400, Federal Products Corporation, Providence, R.I., fitted with a 250 mg universal probe with a high resolution probe tip (2.5 micron styles) operated according to the procedure set forth in the instructions furnished by the manufacturer, each reading is a single pass of the instrument over the surface. The settings were:

| | | | |
|---|---|---|---|
| CUTOFF (r) | 0.800 nm | CUTOFF (w) | 0.800 nm |
| FILTER | ANSI 2-RC | DRIVE SPEED | 2.5 nm/sec |
| PROBE RANGE | +/− 500 Um (L) | POLARITY | Normal |
| TRAVERSE | TL | | |

The readings were:

| Substrate | Evaluation Length mm | Ra | Ry |
|---|---|---|---|
| Untreated Untextured (smooth) | 10 | 0.3 | 2.2 |
| | 20 | 0.3 | 2.8 |
| | 40 | 0.3 | 4.0 |
| | 40 | 0.3 | 3.8 |
| | 75 | 0.3 | 7.6 |
| Treated Textured (rough) | 20 | 5.3 | 42.2 |
| | 20 | 5.3 | 42.2 |
| | 40 | 5.7 | 43.0 |
| 1. Plastic Tray | 13 | 1.1 | 12.4 |
| 2. Plastic Tray | 13 | 1.5 | 10.6 |
| 3. RIM-LOCK ® Tray | 13 | 0.5 | 4.4 |

Plastic Trays 1 and 2 were randomly chosen perforated plastic trays of unknown origin while tray number 3 was a RIM-LOCK® size 46 brass tray electroplated with nickel and not perforated, a product of the L. D. Caulk Division, Dentsply International Inc.

EXAMPLE 3

A test designed to evaluate the adhesion provided by the invention was carried out. Aluminum sheet was prepared as described in EXAMPLE 2. Test specimens were prepared consisting of two aluminum strips 0.95 mm thick by 25 mm wide by 100 mm long. The method used was holes were drilled in some of the strips with a powered drill to a size of 1/16 inch diameter and 6 holes per square inch. The strips were bonded together over a 625 mm$^2$ area with dental impression material as designated in the chart.

Five different substrate types were evaluated; smooth (S), smooth with holes (SH), smooth coated with Caulk® Tray Adhesive (SA) which is a pressure sensitive silicone adhesive, rough texture prepared as described in EXAMPLE 2 but without holes (R), and rough texture prepared as described in EXAMPLE 2 with holes (RH) added after the rough texture was applied. Four combinations of these five substrates were tested—S/R, SH/RH, R/R, and R/SA.

The method used was the lap shear test method described in ASTM Test D816-55, Method B for rubber cement was used varied only as to the gauge of metal and length of metal strips which are set out below.

The results were:

| Test No. | Impression Material | Test Config. | Max lbs Force Ave. Std.Dev. | Failure Mode Type & Location |
|---|---|---|---|---|
| 1. | Quixx ™ Putty | S/R | 4.8 +/− (na) | A 100% S |
| 2. | Jeltrate ® Plus | S/R | 6.20 +/− 2.9 | M 23%C S 77%A |
| 3. | Polyjel ® NF ™ | S/R | 16.0 +/− 5.0 | A 100% S |
| 4. | Quixx ™ Putty | SH/RH | 8.7 +/− 0.9 | A 100% S |
| 5. | Jeltrate ® Plus | SH/RH | 8.5 +/− 2.7 | M 23%C S |
| 6. | Polyjel ® NF ™ | SH/RH | 17.6 +/− 0.5 | A 100% S |
| 7. | Quixx ™ Putty | R/R | 16.7 +/− 1.5 | A 100% R |
| 8. | Jeltrate ® Plus | R/R | 9.2 +/− 8.0 | A 100% R |
| 9. | Polyjel ® NF ™ | R/R | 41.0 +/− 13.5 | A 100% R |
| 10. | Quixx ™ Putty | R/SA | 18.9 +/− 3.1 | A 100% R |
| 11. | Jeltrate ® Plus | R/SA | 0.0 +/− na | A 100% SA |
| 12. | Polyjel ® NF ™ | R/SA | 9.4 +/− 1.6 | A 100% SA |

A = adhesive failure
M = Mixed adhesive and cohesive failure
C = cohesive failure - cohesive means failure within the dental impression material itself.

In Test No. 2 the failure was M (mixed) 23% cohesive failure and 77% adhesive failure and the adhesive failure was at the smooth surface without holes.

The test results are summarized qualitatively as follows:
TEST 1–6: S/R and SH/RH Specimens All specimens failed at the smooth texture or the smooth texture with holes.

Quixx Putty and Polyjel NF yields 100% adhesive failure at both the S and SH surfaces.

Jeltrate Plus specimens yielded partial failure at both the R and S surfaces.

Specimens with holes yielded lap shear results somewhat higher than those without holes, however, all failure sites remain on smooth surface with or without holes.

TEST 7–12: R/R and R/SA Specimens

The relative ranking (best to worst) of adhesion to the rough (R) texture is Polyjel NF>>Quixx Putty>moist Jeltrate Plus.

The force required to remove Quixx Putty from the rough texture is equal within experimental error, to the force needed to remove Quixx Putty from a smooth texture coated with Caulk Tray Adhesive.

Both Polyjel NF and moist Jeltrate Plus adhere better to the rough texture than they do to the adhesive coated surface.

It has been observed that the rough textured surface is not unpleasing and uncomfortable to dental patients nor does the insertion of the tray over the soft mucosa of the oral cavity even where there is substantial contact with the inside of the lip, produce irritation from present observations. This is true even when the outside body of the tray has the same basic microscopically rough texture as the inside body of the tray.

The dental impression tray of the present invention is inexpensive to manufacture and provides what is considered by the inventors to be clinically optimal retention of the impression material every time. The impression material is locked onto all interior surfaces of the impression tray by multitudes of tiny undercuts in the most preferred embodiment. The impression material does not pull away from any area of the impression tray. The rough surface of the handle makes it non-slip even for a gloved hand. In preferred embodiments the impression tray does not flex and distort the impression. In some of its most preferred embodiments the impression tray is to be so inexpensive that the dentist should use it one time only and thereby eliminate the danger of cross-contamination. In its most preferred embodiments it is also easily recyclable so as to avoid ending up in a landfill. Furthermore, in preferred embodiments the impression tray is easily mass-produced, providing the dentist with the first one-time use impression tray with no sacrifice of impression quality.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific embodiments discussed in detail herein.

It is claimed:

1. A dental impression tray comprising dental impression material adhering surfaces comprising a multiplicity of microscopic randomly disposed pits having undercut and overhanging portions at said surfaces with respect to nominal diameters of said pits.

2. The dental impression tray of claim 1 wherein said tray is made of readily malleable metal.

3. The dental impression tray of claim 2 wherein said metal is aluminum.

4. The dental impression tray of claim 1 wherein said tray is made from a material selected from the group consisting of plastic, ceramic, metal or more than one of the recited materials in combination.

5. The dental impression tray of claim 1 wherein said adhering surfaces extend over at least 10% of the surfaces of said tray that are intended to be contacted with dental impression material during dental impression taking.

6. The dental impression tray of claim 1 wherein said adhering surfaces comprise a microscopically rough texture comprising a profilometer Ra reading of at least 2.

7. A dental impression tray having tray wall surfaces comprising a microscopically rough texture for adhering a dental impression material thereto, comprising pits having undercut subsurface portions that in their smallest surface diameters are less than 100 microns, said microscopically rough surfaces having a profilometer Ra value of at least about 3.

8. The dental impression tray of claim 7 wherein said microscopic rough texture extends over substantially all of the tray walls that are intended to interface with dental impression material and said walls have a plurality of holes penetrating therethrough.

9. The dental impression tray of claim 7, said tray comprising aluminum.

10. A method of forming a dental impression in polymerizable flowable dental impression material capable of being rendered permanently elastomeric to form a mold shape having a memory, comprising:

a. placing a predetermined quantity of said flowable dental impression material in a dental impression tray having walls defining a recess for receiving said material, said walls comprising microscopically roughened texture having a profilometer Ra value of at least about 2, comprising a multiplicity of microscopic randomly disposed pits having undercut and overhanging portions at said surfaces with respect to nominal diameters of said pits, on said dental impression tray walls that are intended to interface with dental impression material;

b. inserting said impression tray in the oral cavity and impressing said material in said tray against dental anatomy in the oral cavity to form a desired mold; and c. removing said mold from the oral cavity, after said dental impression material has cured to a permanently elastomeric mold, said impression material adhered by said microscopically roughed texture to said walls of said dental impression tray.

11. The method of claim 10, wherein said adhering of said mold to said dental impression tray comprising micro mechanical interlocking between said mold and said tray walls having said microscopically roughened surfaces.

12. A method of manufacturing a dental impression tray comprising sand blasting at least a portion of a surface that is to be an impression material contacting portion of said dental impression tray until said surface yields a profilometer Ra reading of at least 2.

13. The method of claim 12 wherein said sand blasting is done until a portion of said surface yields a profilometer Ra reading of at least 4.

14. The method of claim 12 wherein said sand blasting comprises using an abrasive aluminum oxide.

* * * * *